(12) United States Patent
Herrera et al.

(10) Patent No.: US 10,743,975 B2
(45) Date of Patent: *Aug. 18, 2020

(54) URINARY PROSTHESIS SYSTEMS

(71) Applicant: Spinal Singularity, Inc., San Clemente, CA (US)

(72) Inventors: Derek Herrera, San Clemente, CA (US); Zach McKinney, San Clemente, CA (US); Linh Dinh, San Clemente, CA (US); Prescott Traversi, San Clemente, CA (US)

(73) Assignee: Spinal Singularity, Inc., San Clemente, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 15/721,096

(22) Filed: Sep. 29, 2017

(65) Prior Publication Data

US 2018/0036107 A1  Feb. 8, 2018

Related U.S. Application Data

(60) Division of application No. 15/419,948, filed on Jan. 30, 2017, now Pat. No. 9,775,698, which is a
(Continued)

(51) Int. Cl.
  *A61F 2/00* (2006.01)
  *A61F 2/48* (2006.01)

(52) U.S. Cl.
  CPC .......... *A61F 2/0027* (2013.01); *A61F 2/0022* (2013.01); *A61F 2002/48* (2013.01);
(Continued)

(58) Field of Classification Search
  CPC ............................................. A61F 2/0022–004
  See application file for complete search history.

(56) References Cited

U.S. PATENT DOCUMENTS

| 3,812,841 A | 5/1974 | Isaacson |
| 4,168,699 A | 9/1979 | Hauser |

(Continued)

FOREIGN PATENT DOCUMENTS

| EP | 1096900 | 9/2005 |
| EP | 2094343 | 10/2017 |

(Continued)

OTHER PUBLICATIONS

EPO; Supplemental Search Report and Written Opinion dated Jan. 2, 2018 in EP 16740891.3.
(Continued)

*Primary Examiner* — Thaddeus B Cox
(74) *Attorney, Agent, or Firm* — Snell & Wilmer L.L.P.

(57) ABSTRACT

The disclosure relates generally to an extended use systems and devices for management of bladder function for people with urinary dysfunction. The system includes a prosthesis which can include a retaining portion to prevent migration and a valve that can control fluid flow. The catheter can be placed inside the bladder using devices that facilitate insertion and extraction. The placement of the catheter can be done by a trained individual such as a patient, as well as a clinician, a nurse, or a caretaker. Once placed inside the bladder, the catheter can be fully-internal, meaning no portion of the catheter is visible from outside of the patient's body.

6 Claims, 9 Drawing Sheets

Related U.S. Application Data continuation-in-part of application No. PCT/US2016/014648, filed on Jan. 23, 2016.

(60) Provisional application No. 62/107,203, filed on Jan. 23, 2015.

(52) U.S. Cl.
CPC . *A61F 2210/009* (2013.01); *A61F 2220/0033* (2013.01); *A61F 2250/0002* (2013.01); *A61F 2250/0003* (2013.01); *A61F 2250/0013* (2013.01)

(56) References Cited

U.S. PATENT DOCUMENTS

| | | | |
|---|---|---|---|
| 4,932,938 | A | 6/1990 | Goldberg |
| 5,041,092 | A | 8/1991 | Barwick |
| 5,366,506 | A | 11/1994 | Davis |
| 5,380,268 | A | 1/1995 | Wheeler |
| 5,411,507 | A | 5/1995 | Heckele |
| 5,476,434 | A | 12/1995 | Kalb et al. |
| 5,628,770 | A | 5/1997 | Thome et al. |
| 5,713,877 | A | 2/1998 | Davis |
| 6,053,897 | A | 4/2000 | Sachse |
| 6,066,088 | A | 5/2000 | Davis |
| 6,132,365 | A | 10/2000 | Sigurdsson |
| 6,527,702 | B2 | 3/2003 | Whalen |
| 6,565,536 | B1 | 5/2003 | Sohn |
| 6,602,243 | B2 | 8/2003 | Noda |
| 6,638,208 | B1 | 10/2003 | Ananth et al. |
| 6,835,183 | B2 | 12/2004 | Lennox et al. |
| 7,001,327 | B2 | 2/2006 | Whalen |
| 7,147,606 | B1 | 12/2006 | Chang et al. |
| 7,338,028 | B2 | 3/2008 | Zimmerling et al. |
| 7,415,308 | B2 | 8/2008 | Gerber et al. |
| 7,803,106 | B2 | 9/2010 | Whalen et al. |
| 8,801,697 | B2 | 8/2014 | Yugari |
| 8,882,652 | B2 | 11/2014 | Vitzthum |
| 9,011,314 | B2 | 4/2015 | Davis et al. |
| 9,452,278 | B2 | 9/2016 | Davis et al. |
| 9,775,698 | B2 | 10/2017 | Herrera et al. |
| 2002/0165427 | A1 | 11/2002 | Yachia et al. |
| 2003/0229263 | A1 | 12/2003 | Connors et al. |
| 2004/0019369 | A1 | 1/2004 | Duncan et al. |
| 2004/0106899 | A1 | 6/2004 | McMichael et al. |
| 2005/0216069 | A1 | 9/2005 | Cohen et al. |
| 2006/0020297 | A1 | 1/2006 | Gerber |
| 2006/0184090 | A1 | 8/2006 | Davis et al. |
| 2006/0247723 | A1 | 11/2006 | Gerber et al. |
| 2008/0269546 | A1 | 10/2008 | Wilkie et al. |
| 2008/0294069 | A1 | 11/2008 | Stickler et al. |
| 2009/0157053 | A1 | 6/2009 | Davis et al. |
| 2010/0234876 | A1 | 9/2010 | Watson |
| 2010/0312225 | A1 | 12/2010 | Armistead |
| 2011/0054404 | A1 | 3/2011 | Tanabe et al. |
| 2011/0066139 | A1 | 3/2011 | Winegar |
| 2012/0316584 | A1 | 12/2012 | Miles |
| 2013/0041430 | A1 | 2/2013 | Wang et al. |
| 2013/0090630 | A1 | 4/2013 | Winegar |
| 2014/0148648 | A1 | 5/2014 | Tycast et al. |
| 2014/0213979 | A1 | 7/2014 | Boyco et al. |
| 2014/0214009 | A1 | 7/2014 | Reyes |
| 2014/0371803 | A1 | 12/2014 | Grill et al. |
| 2015/0087896 | A1 | 3/2015 | Wei et al. |
| 2015/0366462 | A1 | 12/2015 | Ramos et al. |
| 2016/0000641 | A1 | 1/2016 | Driscoll et al. |
| 2017/0156838 | A1 | 6/2017 | Herrera |
| 2018/0140799 | A1 | 5/2018 | Herrera |
| 2018/0153669 | A1 | 6/2018 | Herrera |
| 2018/0153670 | A1 | 6/2018 | Herrera |
| 2018/0153671 | A1 | 6/2018 | Herrera |

FOREIGN PATENT DOCUMENTS

| | | |
|---|---|---|
| EP | 3247309 | 11/2017 |
| WO | 2000002499 | 1/2000 |
| WO | 2001010358 | 2/2001 |
| WO | 2011032150 | 3/2011 |
| WO | 2016118943 | 7/2016 |
| WO | 2017172998 | 10/2017 |
| WO | 2019068104 | 4/2019 |

OTHER PUBLICATIONS

International Preliminary Report on Patentability dated Jul. 25, 2017 in PCT/US2016/014648.
Mexico; Non-Final Office Action dated Jan. 26, 2018 in MX2017-009517.
PCT; Written Opinion dated Jul. 25, 2016 in International Application No. PCT/US2016/014648.
USPTO; Final Office Action dated Mar. 25, 2019 in U.S. Appl. No. 15/072,345
Non-Final Office Action dated Oct. 23, 2018 in U.S. Appl. No. 15/072,345.
PCT; International Preliminary Report on Patentability dated Oct. 2, 2018 in International Application No. PCT/US2017/024862.
Notice of Allowance dated Aug. 17, 2017 in U.S. Appl. No. 15/419,948.
Final Office Action dated Jul. 13, 2017 in U.S. Appl. No. 15/419,948.
Office Action dated Jun. 16, 2017 in U.S. Appl. No. 15/419,948.
Restriction Requirement dated Mar. 23, 2017 in U.S. Appl. No. 15/419,948.
Restriction Requirement dated Jul. 5, 2018 in U.S. Appl. No. 15/072,345.
PCT; International Search Report dated Jul. 25, 2016 in International Application No. PCT/US2016/014648.
PCT; International Search Report dated Aug. 17, 2017 in International Application No. PCT/US2017/024862.
PCT; Written Opinion dated Aug. 17, 2017 in International Application No. PCT/US2017/024862.
AUIPO; Office Action dated Jul. 22, 2019 in Australian Application No. 2016209038.
USPTO; Non-Final Office Action dated Aug. 26, 2019 in U.S. Appl. No. 15/877,228.
USPTO; Non-Final Office Action dated Sep. 12, 2019 in U.S. Appl. No. 15/785,405.
USPTO; Non-Final Office Action dated Sep. 13, 2019 in U.S. Appl. No. 15/072,345.
USPTO; Non-Final Office Action dated Sep. 13, 2019 in U.S. Appl. No. 15/785,403.
EPO; Supplementary European Search Report dated Jan. 19, 2018 in EP16740891.3.
PCT; International Search Report dated Jan. 28, 2019 in International Application No. PCT/US2018/053806.
PCT; Written Opinion dated Jan. 28, 2019 in International Application No. PCT/US2018/053806.
USPTO; Restriction Requirement dated Aug. 9, 2019 in the U.S. Appl. No. 15/877,228.
USPTO; Final Office Action dated Dec. 6, 2019 in the U.S. Appl. No. 15/877,228.
USPTO; Final Office Action dated Jan. 30, 2020 in the U.S. Appl. No. 15/785,403.
USPTO; Notice of Allowance dated Feb. 5, 2020 in the U.S. Appl. No. 15/072,345.
USPTO; Final Office Action dated Feb. 12, 2020 in the U.S. Appl. No. 15/785,405.
USPTO; Notice of Allowance dated Apr. 23, 2020 in the U.S. Appl. No. 15/877,228.
USPTO; Notice of Allowance dated Apr. 24, 2020 in the U.S. Appl. No. 15/785,398.
UK; Office Action dated Feb. 5, 2020 in UK. Application No. GB1713519.3.

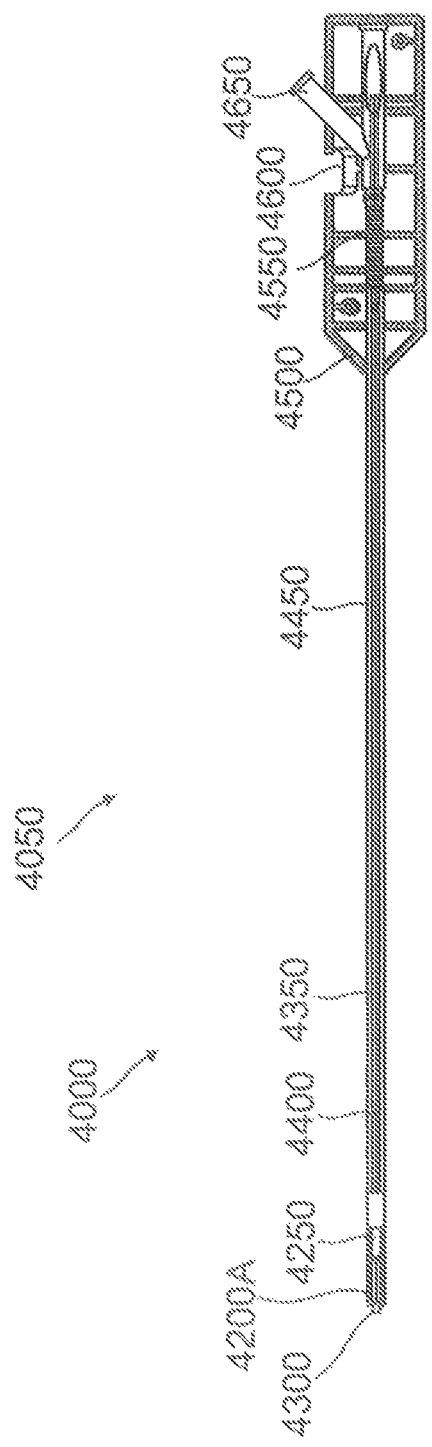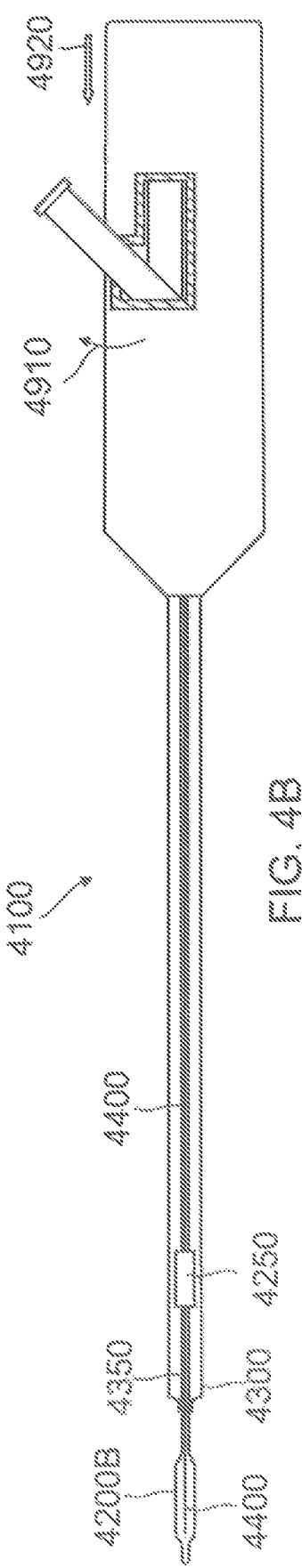

URINARY PROSTHESIS SYSTEMS

CROSS-REFERENCE TO RELATED APPLICATIONS

This application is a divisional of and claims priority to U.S. patent application Ser. No. 15/419,948 (now U.S. Pat. No. 9,775,698), filed Jan. 30, 2017 which is a continuation-in-part of, and claims priority to, PCT application Ser. No. PCT/US2016/014648, which claims priority to U.S. Provisional Pat. App. Ser. No. 62/107,203, filed Jan. 23, 2015, titled "WIRELESS PRESSURE SENSOR," the contents of each of which are incorporated by reference herein in their entirety.

FIELD

This disclosure generally relates to bladder management systems, and in particular, urinary prosthesis systems and delivery devices.

BACKGROUND

Currently, there are a significant number of people who suffer from neurogenic lower urinary tract dysfunction, also commonly known as neurogenic bladder. Neurogenic bladder can be defined as impaired urinary function due to neurological injury or disease such as spinal cord injury (SCI). The current standard of care for management of chronic urinary retention disorders such as neurogenic bladder is to drain the bladder using intermittent catheterization (IC) or indwelling Foley catheters. Current methods however are associated with high rates of urinary tract infection and gensto-urinary (GU) injury, both of which significantly diminish the patient's quality of life. Furthermore, because individuals with neurogenic bladder commonly lack bladder sensation and thus cannot accurately perceive bladder fullness, many are susceptible to bladder over-filling resulting in urinary "accidents" and/or urinary reflux which presents a high risk of both infection and tissue damage to the upper urinary tract. To avoid these outcomes, individuals with neurogenic bladder on IC programs commonly rely on a timed catheterization schedule. This approach is imprecise and may call for catheterization more frequently than necessary, further increasing the risk of infection and GU injury. Therefore, it is desirable to provide an improved urinary prosthesis that overcomes most, if not all, of the preceding problems. A fully-internal, semi-permanent urinary prosthesis that enables voluntary bladder voiding without the need for IC or external drainage bags could significantly decrease medical complication rates while improving the comfort and convenience of urinary management for many individuals with neurogenic bladder. A urinary prosthesis device having a valve that is fully internal to the users body, which also allows the user to open and close the valve from outside the body, would significantly reduce the frequency of foreign objects entering the urethra, thereby lowering the risk of infection and/or GU injury. A urinary prosthesis having a retention mechanism resting in the user's bulbar urethra can aid in proper placement of the prosthesis and reduce migration of the prosthesis once placed. A urinary prosthesis device having an atraumatic retention mechanism can aid in reduced risk of infection to the users body. A urinary prosthesis device shaped and sized to house one or more sensors within the prosthesis can aid in accurate reading by the sensors to collect data. A urinary prosthesis device housing one or more sensors and properly placed in the users body can prevent displacement of sensors and prevent trauma to the users body. A urinary prosthesis device adapted to house sensors and be placed inside a user's body for an extended period of time can aid with consistent reading of data, e.g. pressure, pH, volume of urine, etc. A urinary prosthesis device adapted to place a sensor in a consistent location within the users body can integrate with other medical apparatuses, e.g. CT, ultrasound, x-ray, electronic data storage devices, etc. A urinary prosthesis device having sensors can aid in collection of data while being used with external devices, e,g. sensors placed in toilets, etc. Further, if such a prosthesis could be periodically inserted, removed, and replaced by the user without medical visits or the aid of another individual, the user would save additional time and medical expenses while avoiding discomfort and inconvenience. A delivery (insertion) device with a mating structure that firmly connects to the urinary prosthesis can allow a user to conveniently manipulate and accurately place the catheter inside the users body without requiring auditory and visual feedback.

SUMMARY

The present technology relates to systems and methods for controlling urinary function and, in particular, a urinary prosthesis system for extended use bladder management.

BRIEF DESCRIPTION OF THE DRAWINGS

The following drawings and the associated descriptions are provided to illustrate the present disclosure and do not limit the scope of the claims.

FIGS. 4A-4C show schematic drawings of an embodiment of a sample delivery system.

DETAILED DESCRIPTION

Disclosed herein are embodiments of systems that can be used for bladder management in patients with urinary retention disorders, including neurogenic bladder. For example, embodiments of the system can be used to control the amount of urine inside a person's, or an animal's, bladder and/or the pressure of urine in the bladder. However, the disclosed systems can be used for fluid flow control for other bodily organs as well, and the particular bodily organ described is not limiting. The disclosed systems can also be used for obstructive disorders, whereby the flow of urine from the bladder is physically impeded, for instance, by a urethral stricture or enlarged prostate gland. As used herein, the term "user" is intended to include any person trained and able to perform the prosthesis insertion and removal procedure, including the patient, doctor, caregiver, nurse, etc. The term "patient" and "individual" are intended to be interchangeable. The term "body" used herein is defined as "an animate body" including human, animal, and the like. The term "lower urinary tract" refers collectively to the urinary bladder and urethra. The term "extended use" herein refers to use of prosthesis for an extended period, without requiring the prosthesis to be taken out of the body for more than once every two days. For example, a prosthesis used in a patient for two weeks before being replaced is considered an extended use prosthesis. The term "distal" refers to a direction relatively furthest from the patient using a prosthesis described herein. For example, the end of a prosthesis placed within the body of the patient is considered a proximal end of the prosthesis, while the prosthesis end being inserted last into the patient during insertion and placement of the prosthesis is a distal end of the prosthesis. Unless otherwise indicated, "Lumen Diameter," as used herein in connection with a prosthesis, shall mean the diameter of a circle within the same cross-sectional area of a lumen of a prosthesis component. For example, if a prosthesis has an oval lumen with cross-sectional area of 1 mm$^2$, the Lumen Diameter is the diameter of a circle with cross-sectional area of 1 mm$^2$. The term "proximal" refers to a direction relatively closer to the body of the patient using a prosthesis described herein. For example, the end of a prosthesis placed within the body of the patient is considered a proximal end of the prosthesis, while the prosthesis end being inserted last into the patient during insertion and placement of the prosthesis is a distal end of the prosthesis.

Urinary Prosthesis System

Figure 1:
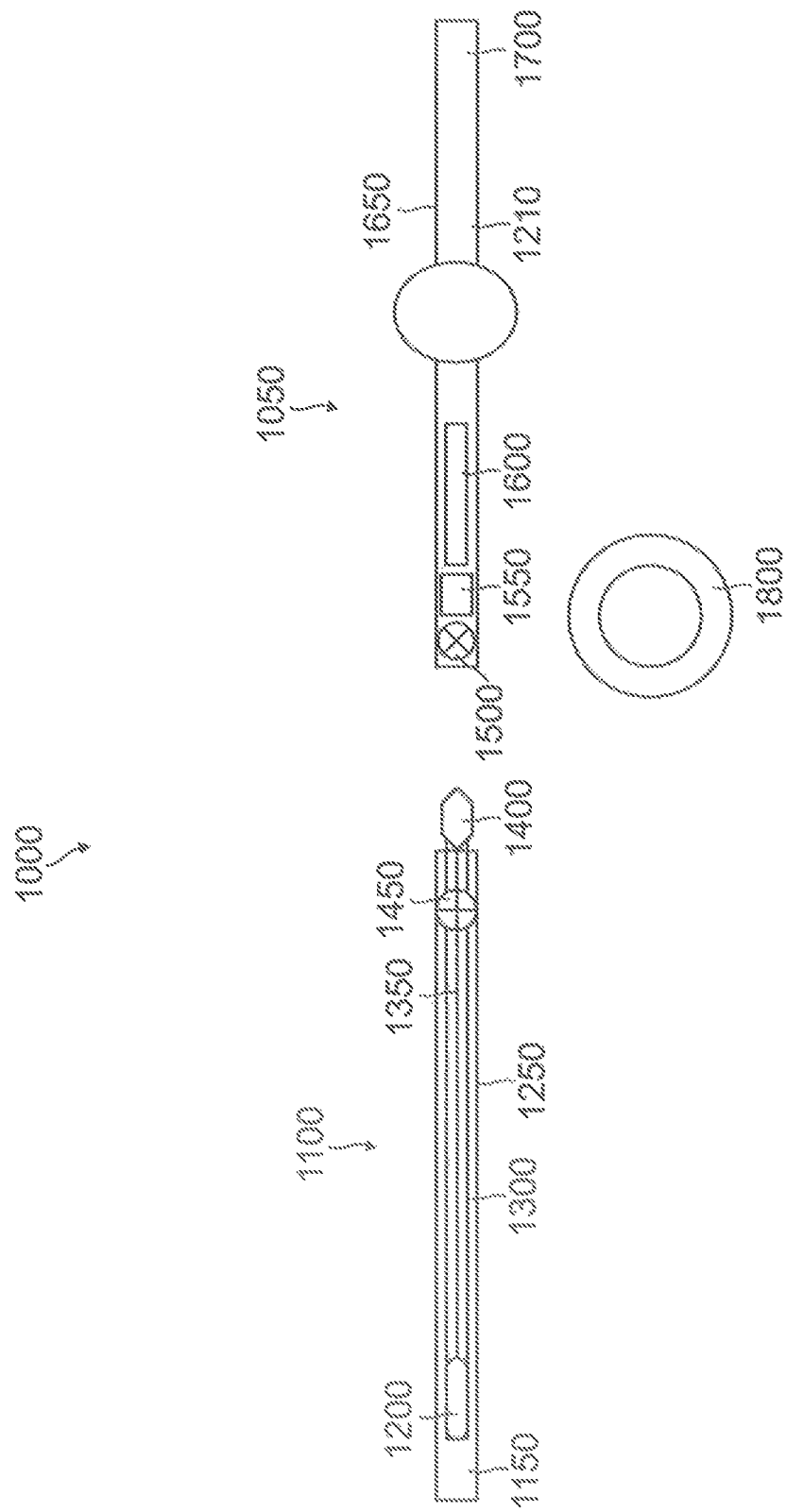
FIG. 1 shows a schematic drawing of a sample urinary prosthesis system.
Figure 2:
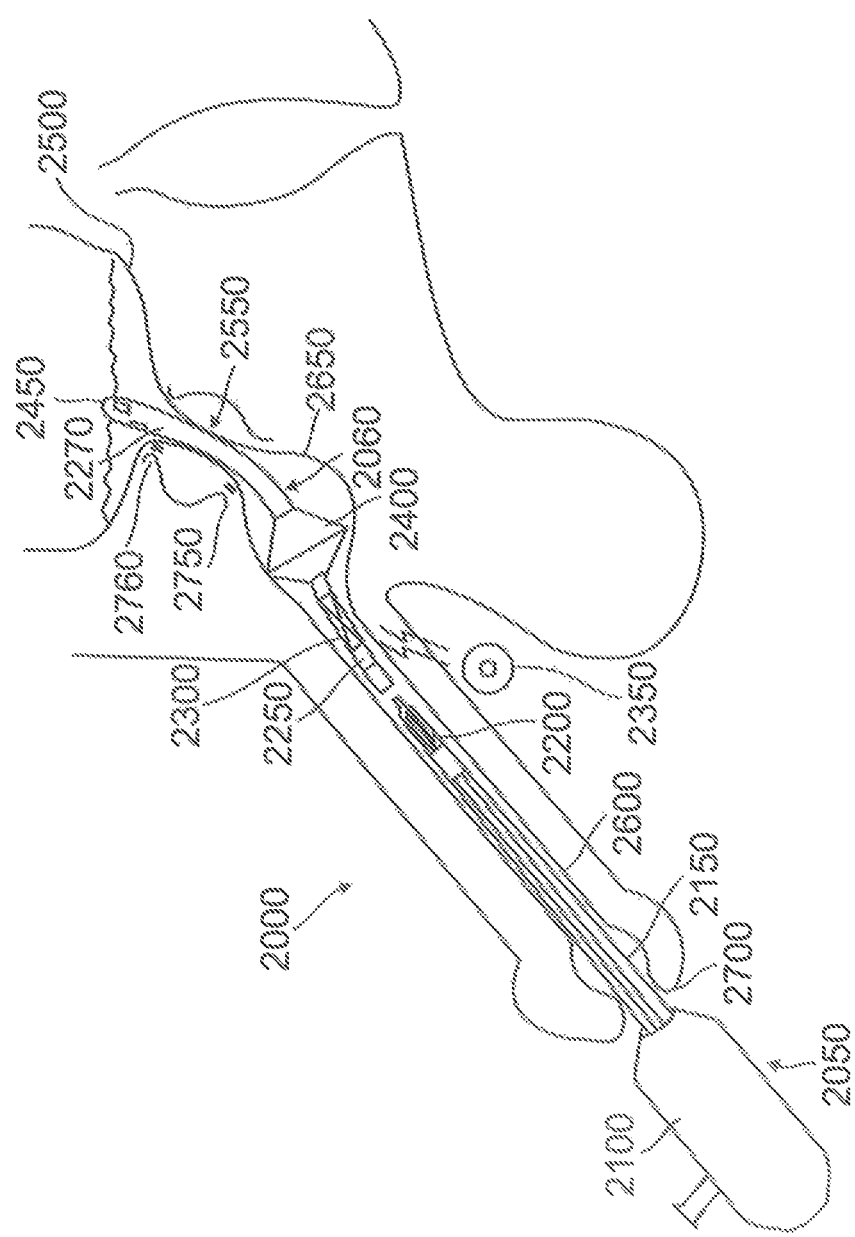
FIG. 2 shows a schematic drawing of a urinary prosthesis system used in a male.

FIG. 1 shows a schematic drawing of a sample urinary prosthesis system. A urinary prosthesis system 1000 can comprise a prosthesis 1050. The prosthesis 1050 can be an extended-extended use catheter. The prosthesis 1060 can be shaped and sized to be introduced into the lower urinary tract of a patient. The prosthesis 1050 can be fully-internal to the body of the patient. Once placed inside the patient, the prosthesis 1050 can extend at least from the bladder past the prostate and external urinary sphincter, as shown in FIG. 2. The prosthesis 1050 can comprise a prosthesis tube 1210, a valve 1600, and a mating structure 1360. The prosthesis tube 1210 can comprise a lumen 1215. The prosthesis 1050 can further comprise a retaining portion 1650, and a proximal tip 1700. The retaining portion 1650 can be configured to prevent migration of the prosthesis within the urethra. For example, the retaining portion 1650 can comprise ribbings, anchors, balloons, shape memory structures, etc. The proximal tip 1700 can be configured to allow inflow of urine from the bladder into the prosthesis lumen. For example, the proximal tip 1700 can comprise holes and/or inlets.

In some embodiments, the bladder management system 1000 can comprise a delivery device 1100, and the prosthesis 1050 can be configured to mate with the delivery device 1100. The delivery device 1100 can comprise a housing 1150 and a tube comprising a lumen 1250. Further, the delivery device 1050 can comprise an enlargeable portion. The enlargeable portion can be configured to mate with the mating chamber portion 3050. For example, the enlargeable portion can comprise ribbings, anchors, balloons, shape memory structures, umbrella, clamp, threads, etc. The enlargeable portion can be a balloon 1400 that mates with a mating chamber 1550 of the prosthesis 1050. The delivery device 1100 can be an endoscope and/or cystoscope. In some embodiments, the urinary prosthesis system 1000 can comprise a fluid inlet 1200. The fluid inlet 1200 can be configured to deliver fluid to the balloon 1400. For example, the fluid inlet 1200 can be connected to an inner lumen 1300 inside the outer lumen 1250 and fluid can be introduced to the fluid inlet 1200 to expand the balloon 1400. The delivery device 1100 can further comprise a mandrel 1350. The mandrel can be configured to advance the balloon into the mating chamber 1550 of the prosthesis.

In some embodiments, the bladder management system 1000 can comprise a mating structure 1360 comprising a first mating magnet 1450 and a second mating magnet 1500. The mating structure 1360 can further comprise a mating chamber 1550 shaped and sized to fit in the mating balloon 1400. The first mating magnet 1450 and the second mating magnet 1500 can be configured to align and mate corresponding portions of the delivery device 1100 and the prosthesis 1050. For example, the magnetic force between the two magnets 1450, 1500 can automatically align the mating balloon 1400 and the mating chamber 1550 automatically when the mating balloon 1400 and the mating chamber 1550 are placed close to each other. The alignment of the magnets 1450, 1500 can be generally concentric to each other.

The prosthesis 1050 can be used to control the flow of urine from the bladder for extended use. For example, the prosthesis 1050 can remain fully inside the body of the patient without having to be manually accessed in order to control the flow of urine. The valve 1600 can be placed along the body of the prosthesis 1050. The valve 1600 can be opened and closed using a wireless control signal from outside the patient's body. The valve 1600 can be configured to control the flow of urine by opening and closing the valve based on input received from an actuator 1800. For example, the valve 1600 can comprise a magnet, and the actuator 1800 can be used to open and close the valve using magnetic force.

The delivery device 1100 can be used to place the prosthesis 1050 in the patient's body. The delivery device 1100 can be used to remove the prosthesis 1050 from the patient's body. In some embodiments, the delivery device 1100 may also be used to open or close the valve 1600. The balloon 1400 of the delivery device 1100 can be placed inside a portion of the prosthesis lumen 1210 and inflated to engage the prosthesis 1050. In some embodiments, a portion of the prosthesis lumen 1210 can comprise a mating chamber configured to engage and/or dis-engage the balloon 1400, based on the balloon's level of inflation. Once engaged, the prosthesis 1050 can be delivered through the urethra, as shown in FIG. 2, by using the delivery device both to advance and/or retract the prosthesis, as necessary.

The prosthesis system 1000 can comprise a computing device. In some embodiments, the computing device can have a software which can be used to interpret the values sent from the sensor. In some embodiments, the sensor is a pressure sensor and the computing device can be used to alert a user about when their bladder is likely to contract and void. In some embodiments, the urine amounts inside the bladder can be calibrated by feedback from the individual user after insertion or implantation. In some embodiments, the sensor can use other spectrums of energy, to include acoustics, to determine the fullness or volume of urine in the bladder. Different types of sensors can be embedded on the catheter to determine important metrics of bladder health including pH, volume, pressure, etc. In some embodiments, this can be accomplished through software that analyzes the sensor response and utilizes machine learning algorithms to predict and interpret this data.

In one embodiment, the sensor can determine the pressure of urine within the bladder and send a signal to the processor. The processor sends information on pressure level in the bladder to the computing device. The computing device, using a software, determines whether urine needs to be drained from the bladder. The computing device will also notify the user to drain urine from the bladder. The user can actuate the valve which will allow urine to leave the bladder. In some embodiments, the sensor can be used to determine when urine has been sufficiently drained from the bladder, such as by determining that the pressure level within the bladder has dropped below a certain level. This information can be used to close the valve and halt the flow of urine from leaving the bladder. This sensing technology is not limited to pressure, and in some embodiments, other metrics can be used to make decisions with clinical impact.

The catheter can be used to determine various conditions within the bladder. The sensor can be a pH sensor, an ultrasonic sensor, a displacement sensor, acoustic sensor, etc. Different types and combinations of sensors can be used. For example, the catheter can comprise a pH sensor and a pressure sensor.

The sensor can be configured to change its mechanical properties (e.g. color, size, shape, etc.) based on pressure changes inside the bladder. The user can use an external device to detect changes in mechanical properties of the sensor by, for example, sending and/or receiving sound waves, light waves, etc. In some embodiments, the internal sensor can function without a power source. By constructing the sensor in a specific manner the external unit can observe changes in the resonant frequency characteristics.

The sensor device can utilize basic wireless transmission protocol to wirelessly send data to a computing device with the control software on it. This can be accomplished in a manner similar to Bluetooth, 802.11 WiFi, SONAR, Ultra-Sound, MedRadio or other wireless communications protocols.

The sensors can be placed within a specific location of the prosthesis. For example, the prosthesis comprising different inner diameters 3300, 3350 can comprise a diameter to fit a specific size sensor such that the sensor does not move within the lumen. The outer wall of the tube can prevent any part of the sensor contacting the body tissue.

The sensors can collect long-term, ambulatory and/or clinical, accurate data. For example, the sensors placed inside extended use prosthesis 3000 can improve data by having consistent sensor location and extended duration of sensors within the body to more constantly monitor patient conditions, without having sensors taken out of the body. The sensors placed inside prosthesis can interface with different devices to provide and store data. For example, the sensors can comprise sensors configured to interface with CT, ultrasound, x-ray, electronic data storage devices, etc.

The external computing device can be wirelessly connected to the valve and the valve is configured to actuate based on data processed by the external computing device. The prosthesis 3000 can provide platform for sensors to stabilize location of sensors within the body, such that location of the one or more sensors remain substantially unchanged while inside the body once the extended use prosthesis is placed inside the body.

The prosthesis 3000 can comprise parts configured to interface and/or communicate with suite of different products. For example, the prosthesis can be configured to interface with Amazon Echo® or Google Home®. The prosthesis can be configured to interface with, for example, urine collection device configured to accurately determine volume of urine, and send and store urine volume data in, for example, patient databases in hospitals.

Extended Use Prosthesis

FIG. 2 shows a schematic drawing of a urinary prosthesis system used in a male lower urinary tract. The urinary prosthesis system 2000 can comprise a delivery device 2050 and a urinary prosthesis 2060. The delivery device 2050 can generally comprise a housing 2100 and a delivery shaft 2150. The delivery device 2050 can further comprise a first mating balloon portion 2200. The prosthesis 2000 can comprise a tubular body 2270, a second mating portion 2250, a valve portion 2300, a retaining portion 2400, and a proximal tip 2450.

The prosthesis can comprise one or more sensors configured to transmit data from the patient's body. The data can comprise one or more of: pressure, volume, temperature, acidity, bacteria, chemical composition, fluid flow. The one or more sensor can be placed along the body of the prosthesis 2060. For example, the sensor can be placed on or near the proximal tip 2450.

As shown in FIG. 2, the prosthesis 2060 can extend from the bladder 2500 to a portion of the urethra 2600 distal to the prostate 2550 and the bulbar urethra 2650. In some embodiments, the prosthesis 2060 extends distal to the prostate and external urinary sphincter 2750. The valve portion 2300 can be positioned distal to the retaining portion 2400. The retaining portion can be positioned distal to the proximal tip 2450. The valve portion 2300 can be configured to restrict or allow flow of fluid from the bladder 2500. For example, the valve portion 2300 can be positioned within a portion of the prosthesis 2060. The valve portion 2300 can be opened or closed using an actuator 2350. For example, the valve portion 2300 can comprise a magnetic valve, and an actuator 2350 can be placed on or near the valve 2300 from outside of the patient's body to operate the valve. In some embodiments, the actuator 2350 is a magnetic actuator.

The retaining portion 2400 can be placed on or near the bulbar urethra 2650 of the patient. The retaining portion 2400 can be configured to prevent inadvertent retrograde and/or inadvertent antegrade migration of the prosthesis 2060. For example, the retaining portion 2400 can comprise a structure having a larger cross-section diameter than the tubular body 2270. The retaining portion 2400 can contact the external sphincter 2750 to prevent inadvertent retrograde migration. The retaining portion 2400 can be shaped and sized to prevent inadvertent migration into the penile portion of the urethra 2600.

As shown in FIG. 2, the delivery shaft 2150 can be configured to enter the patient's body through the urethral orifice 2700 into the urethra 2600, to insert and/or extract the prosthesis 2060 from the body. In the female anatomy, the retaining portion can be positioned within the urethra, between the internal urethral orifice and the external urethral orifice. The retaining portion can be positioned such that it is positioned in the urethra between the internal urethral sphincter and the external urethral sphincter.

Urinary Prosthesis

Figure 3:
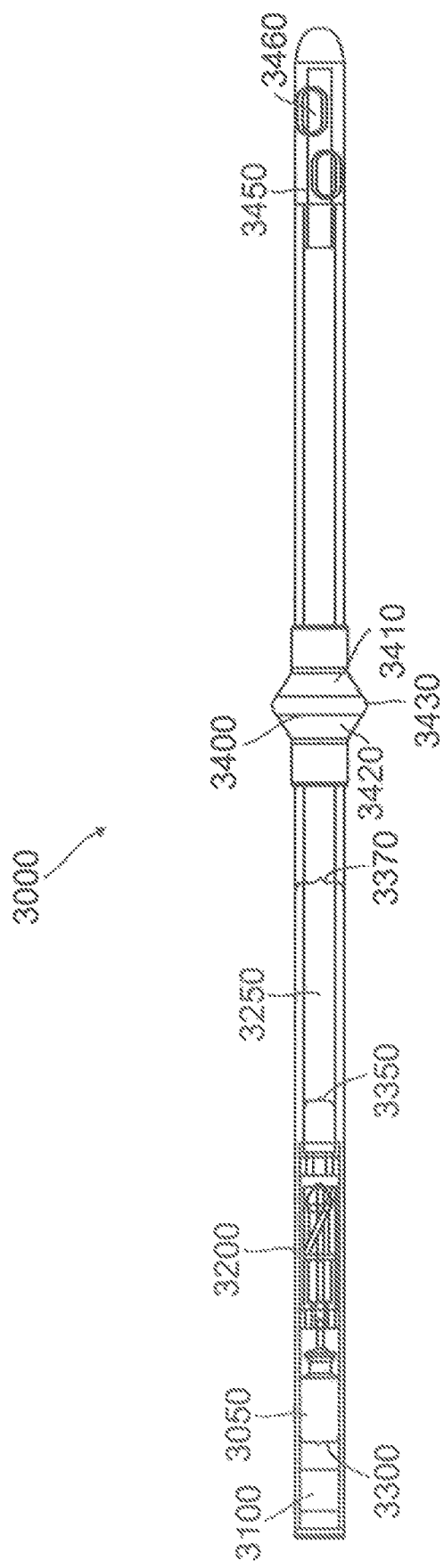
FIG. 3 shows a schematic drawing of an embodiment of a urinary prosthesis.

As shown in FIG. 3, a urinary prosthesis 3000 can comprise a mating chamber portion 3050, a second mating magnet 3100, a valve portion 3200, a prosthesis tube 3250, a retaining portion 3400, and a proximal tip portion 3450. The prosthesis tube 3250 can comprise a lumen having a first lumen profile 3300, a second lumen profile 3350, and tube outer diameter 3370.

The prosthesis tube 3250 will typically have a round or oval cross-sectional shape with an outer diameter ranging from 1 French (0.3 mm) to 20 French (6.6 mm). The lumen comprising lumen profiles 3300, 3350 may have any of a range of cross-sectional geometrical shapes (e.g., circular, oval, semi-circular, rectangular, triangular, trapezoidal, or crescent) and will typically have a cross-sectional surface area equivalent to that of a 0.1 mm diameter circle to a 6.5 mm diameter circle. The first lumen profile 3300 can comprise a cross-sectional surface area greater than the surface area of the second lumen profile 3350. For example, the first lumen profile 3300 can comprise a cross-sectional surface area up to ten times greater than the cross-sectional surface area of the second lumen profile 3350.

The mating chamber 3050 can be on or near the distal tip 3460 of the urinary prosthesis 3000. The mating chamber 3050 can comprise the second lumen profile 3350. The mating chamber 3050 can comprise a space configured to mate with the balloon portion 4200 as shown in FIG. 4. The mating chamber 3050 can be located between the second mating magnet 3100 and the valve portion 3200, The second mating magnet 3100 can comprise an annular, cylindrical shape. The second mating magnet 3100 can be on or near the distal tip 3460 of the urinary prosthesis 3460. The second mating magnet 3100 can comprise an inner diameter greater than deflated diameter of the balloon portion 4200A, 4200B, 4200C. The second mating magnet 3100 can comprise an outer diameter same as or less than the second lumen profile 3350. The second mating magnet 3100 can comprise a ferromagnetic material.

The valve portion 3200 can be located between the chamber 3050 and the retaining portion 3400. The valve portion 3200 can comprise an outer diameter same as or less than the second lumen profile 3350. The valve portion can comprise a cylindrical body, described further in reference to FIG. 6 below.

Figure 8:
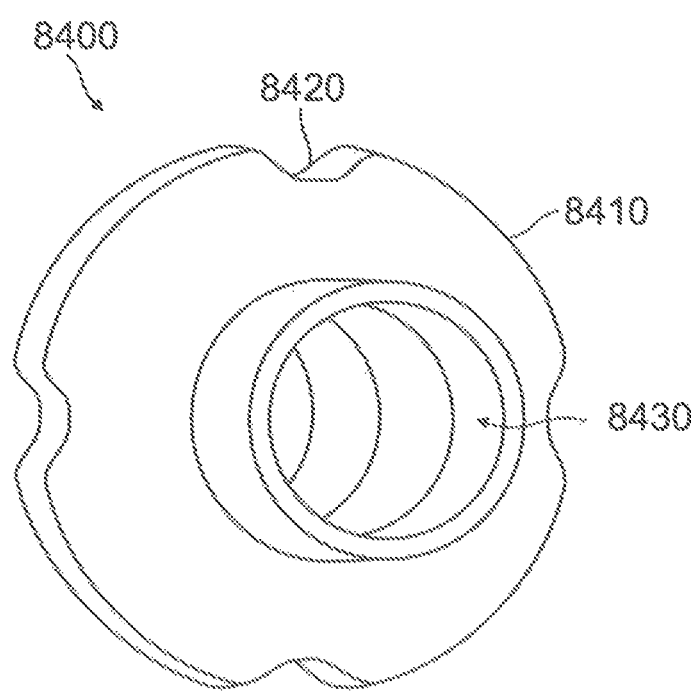
FIG. 8 shows a sample embodiment of a urinary prosthesis retaining portion.

The retaining portion 3400 can be configured to prevent migration of the prosthesis 3000 inside the urethra 2600, as shown in FIG. 2. For example, the retaining portion 3400 can comprise a peak 3430 comprising a cross-sectional dimension greater than the lumen tube outer diameter 3370. The cross-sectional dimension of the peak 3430 can be greater than the cross-sectional dimension of the external sphincter 2750 and smaller than the cross-sectional dimension of the bulbar urethra 2650. The cross-sectional dimension of the peak 3430 can be greater than the penile urethra 2600. The retaining portion 3400 can comprise a proximal tapered surface 3410 and a distal tapered surface 3420. The proximal tapered surface 3410 can comprise a conical surface tapered from the peak 3430 to about the surface of the tube 3250 towards the proximal tip 3450. The distal tapered surface 3420 can comprise a conical surface tapered from the peak 3430 to about the surface of the tube 3250 towards the distal tip 3460. The retaining portion 3400 can comprise a compressible structure. For example, the retaining portion 3400 can comprise a material having softness to compress and pass through smaller lumen diameter than the outer dimension of the peak 3430. The retaining portion 3400 can comprise an air chamber. The cross-sectional geometry of the retaining portion 3400 may comprise non-uniform geometric shapes, e.g. subtractive features. For example, the cross-sectional geometry of the retaining portion 3400 can comprise an iron cross-like shape, as shown in FIG. 8.

The retaining portion 3400 can be atraumatic. The atraumatic retaining portion 3400 can comprise a soft, atraumatic surface. For example, the peak 3430 can comprise a smooth, curved surface. The atraumatic retaining portion 3400 can comprise a flexible silicone material. The atraumatic retaining portion 3400 can comprise soft atraumatic coating. The retaining portion 3400 can be configured to exert a force against wail of bulbar urethra sufficient to prevent migration. The atraumatic retaining portion 3400 can comprise a structure such that no part of the retaining portion 3400 pierces or scrapes tissue of body of a patient.

The urinary prosthesis 3000 can be configured to be inserted and placed inside the urethra of a patient. For example, the prosthesis 3000 can comprise a tube outer diameter 3370 that is the same as or less than the maximum dimension of the urethra 2600. The maximum dimension of the urethra 2600 can comprise the greatest expanded dimension of the urethra 2600. The proximal tip portion 3450 can be configured to enter the urethral orifice 2700 without causing trauma to the body tissue. For example, the proximal tip portion 3450 can comprise a curved tip surface, and a maximum outer dimension equal to, or smaller than, the maximum dimension of the urethra 2600. The proximal tip 3450 can comprise one or more fluid inlets 3460. The one or more fluid inlets 3460 can be configured to receive and pass urine through the prosthesis tube 3250. For example, the one or more fluid inlets 3460 can be placed proximal to the internal sphincter 2760 into the bladder 2500. The proximal tip 3450 can comprise a material with hardness greater than hardness of the lumen 2650.

In some embodiments, the prosthesis 3000 comprises one to six lumen profiles and corresponding number of internal components having different dimensions. For example, a prosthesis comprising three different lumen profiles can comprise a second mating magnet, a valve portion, and a third mating magnet, each comprising a different outer dimension. In some embodiments, the second mating magnet 3100 can comprise a plurality of magnets. For example, a second mating magnet 3100 can comprise a distal magnet, a middle magnet, and a proximal magnet. In some embodiments, the prosthesis 3000 comprises a mating tip. For example, a prosthesis can comprise a mating tip configured to mate with a corresponding portion of a delivery device having a chamber. For example, a prosthesis can comprise a mating tip comprising a deployable mechanism, e.g. balloon, umbrella, etc. In some embodiments, a prosthesis can comprise a deployable mechanism configured to deploy using a delivery device and mate with a corresponding portion on the delivery device.

In some embodiments, the mating chamber 3050 can be located distal to the second mating magnet 3100. In some embodiments, the prosthesis 3000 can comprise a mating structure. The mating structure can include, for example, cutouts, protrusions, ribbings, etc. In some embodiments, the valve portion 3200 can be located between the proximal tip 3450 and the retaining portion 3400. In some embodiments, the retaining portion 3400 can be configured to deploy and/or fold. For example, the retaining portion can comprise a balloon that can be inflated or deflated using a device. In some embodiments, the retaining portion comprising a balloon can be deployed using a delivery device. In some embodiments, the prosthesis 3000 can comprise two or more retaining portions 3400. For example, the prosthesis 3000 can comprise a first retaining portion placed between the proximal tip and the valve portion and a second retaining portion on or near the proximal tip 3450.

In some embodiments, the prosthesis 3000 can comprise a first prosthesis body and a second prosthesis body and a connecting portion. For example, the prosthesis 3000 can comprise a first and second prosthesis bodies comprising tubular bodies and a connecting portion connecting the first and the second prosthesis bodies.

Delivery Device

A urinary prosthesis 3000 can be for extended use rather than requiring dally replacement as some existing devices require. A urinary prosthesis 3000 can be inserted by the patient rather than requiring surgical process as some existing devices require. A urinary prosthesis 3000 can be inserted using tactile feedback rather than requiring auditory and/or visual (e.g. ultrasound, CAT scan, etc.) aid as some existing devices require. The extended use of a urinary prosthesis 3000 can aid in patient comfort, prevent and/or reduce psychological trauma from daily replacement, reduce occurrence of urinary tract infections, etc. The prosthesis 3000 can be extended use because it can be inserted and/or removed by utilizing medical devices, for example, a delivery device 4000. The removal of the prosthesis 3000 can be in a similar manner as when the prosthesis 3000 is implanted within the patient. The delivery device 4000 can comprise structures corresponding to the mating chamber portion 3050 of the prosthesis 3000. The prosthesis 3000 and the delivery device 4000 are designed in such a way that insertion and extraction can be completed by the user.

Insertion

Figure 4C:
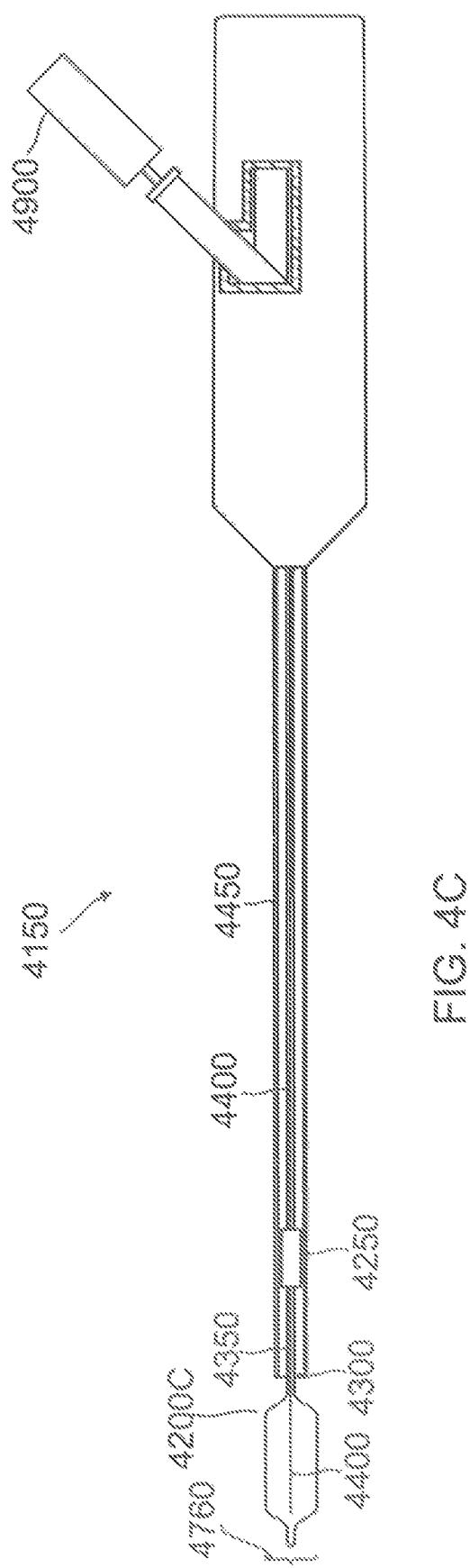

As shown in FIGS 4A-4C, the delivery device 4000 can comprise a housing 4500, an outer lumen 4450, a mandrel 4400, a fluid inlet 4650. The delivery device 4000 can comprise a first mating magnet 4250 and an inner tube 4350.

In the first configuration as shown in FIG. 4A, the balloon 4200A can remain folded. For example, the balloon 4200A can remain folded inside the outer lumen 4450. The lumen 4450 further comprises a device tip 4300. The device tip 4300 can be configured to mate with the second mating magnet 3100. For example, the device tip 4300 can comprise a bottleneck structure that fits in an inner dimension of the second mating magnet 3100 comprising an annular shape. The device tip 4300 can be configured to fit the balloon 4200A. For example, the device tip 4300 can comprise an inner dimension shaped and sized to fit the deflated balloon 4200A.

The housing 4500 can house a portion of the fluid inlet 4650, a portion of the outer lumen 4450, a portion of the inner tube 4350, a portion of the mandrel 4400, and a spring 4550. The housing 4500 can comprise a translucent material, such as translucent PVC. The outer lumen 4450 can comprise a medical grade material, such as nylon. The outer lumen 4450 can comprise a longitudinal length configured to allow the patient to place the prosthesis 3000 in the urinary tract using the delivery device 4000. For example, the outer lumen 4450 can comprise a longitudinal length greater than the penile urethra of a patient. The outer lumen 4450 can comprise a longitudinal length less than or equal to the longitudinal length from the membranous portion to the urethral orifice of a patient, in some embodiments, the outer lumen 4450 can comprise a longitudinal length less than the penile urethra of a patient. The inner tube 4350 can comprise a hollow tube made of a medical grade material, such as nylon. The mandrel 4400 can extend into the balloon 4200A and can comprise a semi-rigid material used in similar medical applications. For example, the mandrel 4400 can comprise Teflon®-coated nitinol or stainless steel wire. The mandrel 4400 can comprise a material having a stiffness which allows bending and flexing without causing trauma to the urethra 2600 while the prosthesis 3000 is being inserted into the patient's body. The mandrel 4400 can comprise a longitudinal length longer than the longitudinal length of the outer lumen 4450.

In some embodiments, a portion of the fluid inlet 4650 can protrude from the housing 4500 through a cutout 4600 on the housing 4500. The fluid inlet 4650 can comprise a switch. The fluid inlet 4650 can be connected to the inner tube 4350 which extends to the balloon 4200. The cutout 4600 can be configured to allow the fluid inlet to move and lock into a second configuration as shown in FIG. 4B. For example, the cutout 4600 can be cut in generally L-shape, such that the protruding portion of the fluid inlet 4650 can move along the L-shaped path to the second configuration (4B). The outer lumen 4450 can be in static connection to the housing 4500 while the spring 4550 exerts a force pushing the fluid inlet 4650 along axis of travel against the outer lumen 4450. The mandrel 4400 can be in static connection to the fluid inlet 4650 and configured to fully extend through the inner tube 4350 and the balloon 4200A, such that by moving the fluid inlet 4650 along the cutout 4600, the balloon 4200A can be exposed outside the lumen 4450.

As shown in FIG. 4B, the delivery device 4000 can be placed in a second configuration where the balloon 4200B is deployed from the lumen 4450. For example, the balloon 4200B can be pushed in and out of the device tip 4300 by moving the fluid inlet 4650 in a longitudinal direction 4920 with respect to the lumen 4450. The balloon can remain outside of the lumen 4450 and the device tip 4300 by rotating 4910 the fluid inlet 4650 in a radial direction along the cutout 4600. The balloon 4200B can be configured to pass through a portion of the prosthesis 3000. For example, the balloon 4200B in a deflated state can be shaped and sized to pass through the inner dimension of the second mating magnet 3100. The mandrel 4400 can comprise a length sufficient to push the balloon 4200B through the inner dimension of second magnet 3100 without causing tears to the balloon 4200B. The inner tube 4350 can be configured to maintain fluid communication with the balloon 4200B in first configuration 4050 and second configuration 4100 of the delivery device 4000 to receive fluid from the fluid inlet 4650.

The balloon 4200C can be inflated by increasing volume of fluid inside balloon, for example by injecting fluid through the fluid inlet 4650. For example, as shown in FIG. 4C a syringe 4900 can be used to pass fluid through the fluid inlet 4650 into the balloon 4200C. The balloon 4200C in inflated state can comprise a generally cylindrical shape having a balloon outer dimension 4760. The balloon 4200C can be configured to fit inside the mating chamber portion 3050. For example, the outer dimension 4760 of the balloon 4760 can comprise a dimension same or less than the first lumen profile 3300. In some embodiments, the outer dimension 4760 of the balloon 4200C can comprise a dimension greater than the first lumen profile 3300. The balloon 4200C can be configured to conform to about 3 atm to about 6 atm in an inflated state. The balloon 4200C can be configured to conform to about 4 atm to about 5.5 atms. The balloon 4200C can comprise a semi-rigid material. For example, the balloon 4200C can comprise polyurethane. In some embodiments, the balloon 4200C can comprise a flexible material, such as rubber. In some embodiments, the balloon 4200C can comprise a non-extensible material such as nylon.

In some embodiments, the device tip 4300 comprises a mating structure. For example, the mating structure can comprise a balloon exposed outside the outer lumen 4450. The balloon may not need to be folded inside the outer lumen. In some embodiments, the device tip 4300 can comprise a mating structure configured to mate with a corresponding structure of a prosthesis. For example, a urinary prosthesis can comprise a mating structure comprising a balloon and the device tip 4300 can comprise a chamber shaped and sized to fit the balloon of the prosthesis.

Mating and Delivery of Prosthesis

The delivery device 4000 and the prosthesis 3000 can be carried in a sterilized pouch. A user may open the pouch comprising a prosthesis 3000 and the delivery device 4000 and insert the prosthesis 3000 into the urethra. The delivery device 4000 can be user-actuated. For example, a user may mate the prosthesis 3000 to the delivery device 4000 before inserting the prosthesis 3000 into orifice 4010. As shown in FIGS. 4A-4C and described above in reference to the figures, the user many manipulate the delivery device 4000 by moving the fluid inlet portion 4660 along the L-shaped cutout 4600 to expose the balloon 4200.

A user may mate the prosthesis 3000 with the delivery device 4000 to retrieve the prosthesis 3000 from the patient's body. For example, lumen 4450 of the delivery device 4000 can be inserted in the urethra of a patient wearing the prosthesis 3000. The second mating magnet 3100 and the first mating magnet 4250 can magnetically attract and align. The user may push the housing 4500 against the prosthesis 3000 to push the balloon 4200 past the second mating magnet 3100. In some embodiments, the user can insert and extract the prosthesis 3000 using the delivery device 4000 to and from the user's body.

Figure 5:
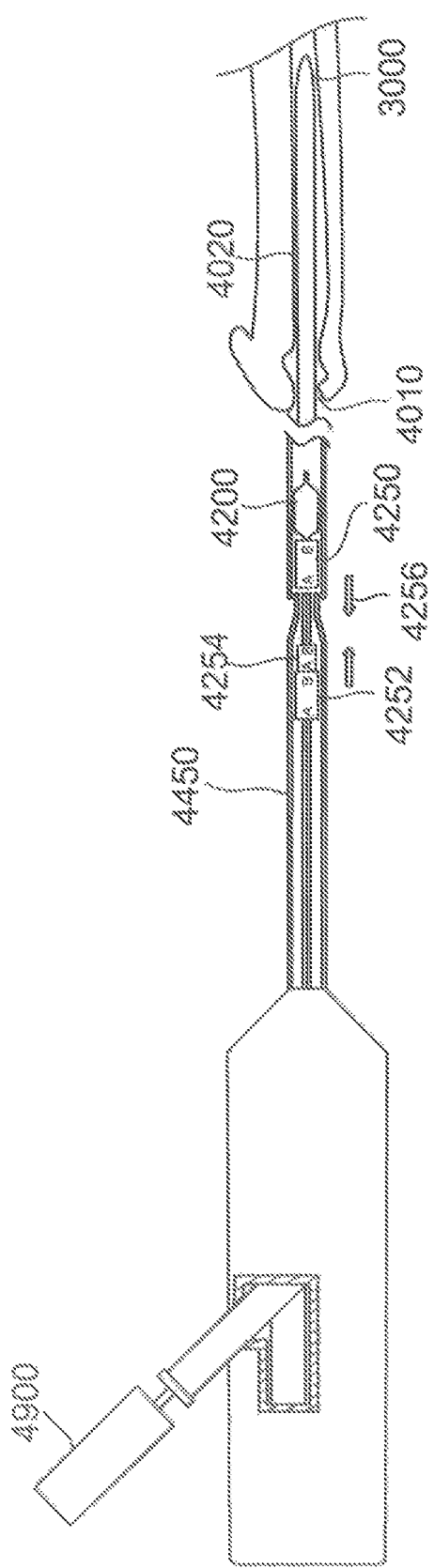
FIG. 5 shows a schematic drawing of an embodiment of a urinary prosthesis mated to a delivery device.

As shown in FIG. 5, the prosthesis system can comprise a mating structure 4005 comprising a plurality of magnets 4250, 4252, 4254 and one or more balloons 4200. A first magnet 4250 can be on the prosthesis 3000. The delivery device 4000 can comprise a proximal mating magnet 4254 and a distal mating magnet 4252. The device 4000 can engagingly mate with the prosthesis 3000. For example, the balloon 4200C can be inflated once inside the chamber 3050 of the prosthesis such that the balloon 4200C can substantially resist the device 4000 from being pulled away and detached from the prosthesis 3000. Once the delivery device 4000 and the prosthesis 3000 are engagingly mated, the user may drag the delivery device to remove the prosthesis 3000 from the patient. The user may dispose the delivery device 4000 and the prosthesis 3000 after removing the prosthesis from the patient's body.

The plurality of magnets 4250, 4252, 4254 can comprise annular cylindrical shapes. The plurality of magnets can be positioned concentrically with each magnet having poles A and B aligned with each other, in a coupled state, in some embodiments, the plurality of magnets 4250, 4252, 4254 can be configured to concentrically align the delivery device lumen 4450 to the prosthesis 3000. For example, the magnets can comprise a smaller magnet 4254 distal to a larger magnet 4252, such that the magnetic pull 4256 can be amplified along the longitudinal axis of the lumen 4450 and the prosthesis 3000.

The placement of the magnets 4250, 4252, 4254 and the balloon 4200 along the longitudinal axes of the delivery device 4000 and the prosthesis 3000 can be changed. For example, an embodiment of a system can comprise a magnet on the delivery device 4000 placed proximal to the balloon 4200. In some embodiments, the system can comprise one to ten magnets. The magnets may have any of a range of cross-sectional geometrical shapes (e.g., circular, oval, semi-circular, rectangular, triangular, trapezoidal, or crescent). The magnets can be placed in a static configuration. In some embodiments, the magnets can be movable inside lumens of prosthesis 3000 and the delivery device 4000. The poles A and B of the magnets can be in decoupled configuration. For example, the magnets 4250, 4252, 4254 can comprise magnets with poles having A-B, B-A, A-B placement respectively along the longitudinal axis of the system 4005. In some embodiments, the magnets 4250, 4252, 4254 can be configured to align the prosthesis 3000 and the delivery device 4000 off the center axes of the prosthesis 3000 and the device 4000. For example, the magnets 4250, 4252, 4254 can be used to move, deflect, bend, or push the prosthesis 3000.

Valve

Figure 6:
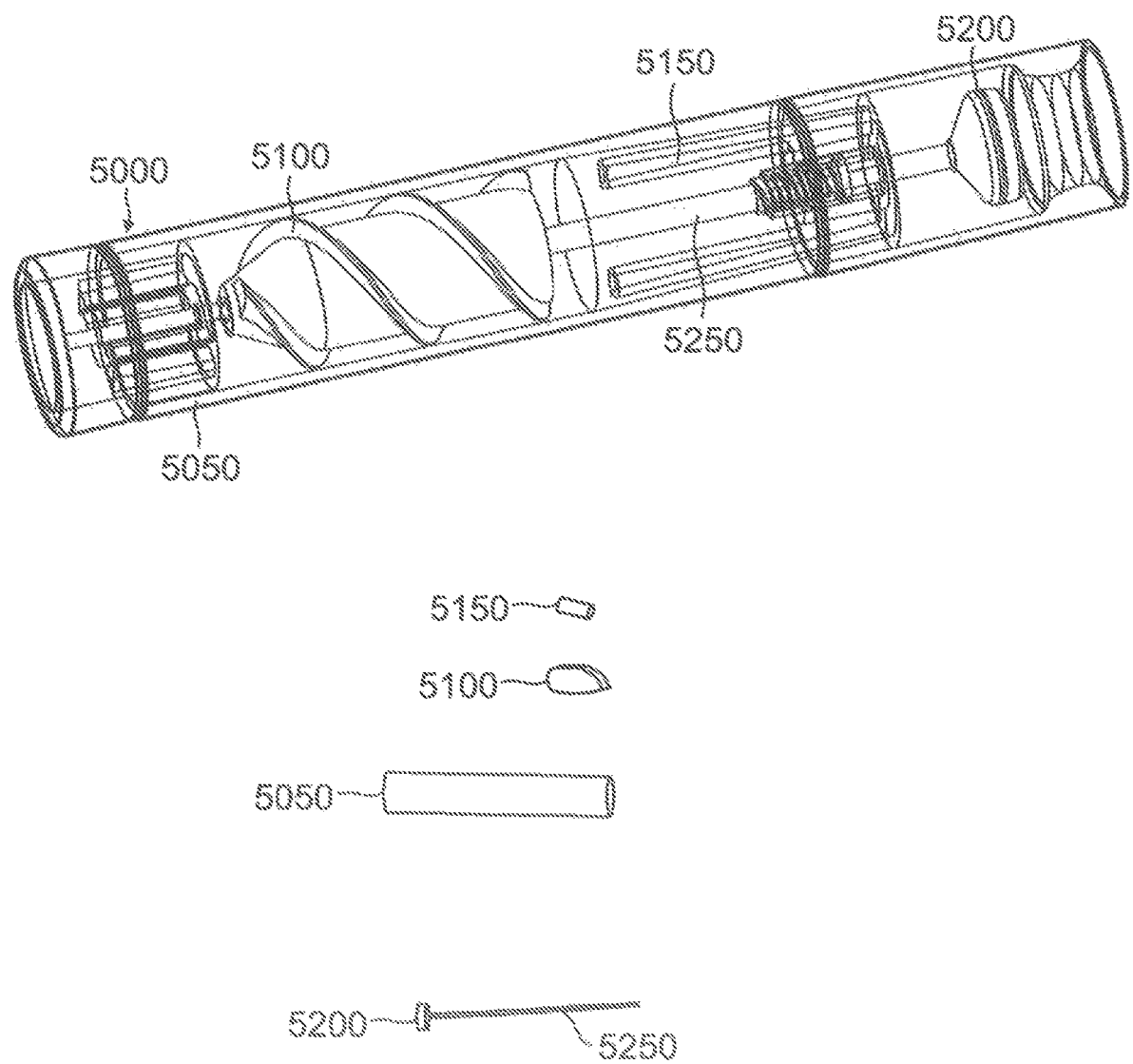
FIG. 6 shows a valve portion of the urinary prosthesis of FIG. 3.

FIG. 6 shows a magnetic valve 5000 used in the urinary prosthesis. The prosthesis 3000 can be configured to maintain a degree of rigidity to rest against the urethra and the prostate sphincter and ensure flow of urine from bladder through the urethra. For example, as shown in FIG. 3, the prosthesis 3000 comprises a first lumen profile 3300 and a second lumen profile 3350 smaller than the first lumen profile. The first lumen profile can house the valve 5000. The second lumen profile 3350 can be configured to provide rigidity against bodily pads once placed inside body of the patient.

As shown in FIG. 6, the valve 5000 can comprise a housing 5050, a screw portion 5100, a valve magnet 5150, a valve tip 5200, a spindle 5250, and an alignment tube 5300. The housing 5050 can comprise a cylindrical body. The screw portion 5100 can comprise a threaded body. The valve tip 5200 can be connected to the spindle 5250. The valve tip 5200 can be configured to open and close the valve. For example, the valve tip 5200 can comprise a conical surface corresponding to the structure of the valve opening.

The screw portion 5100 can be movable inside the housing 5050. The housing 5050 and the screw portion 5100 can be in a threaded connection. The magnet can be connected to the screw portion 5100 and the spindle 5250. By moving the magnet 5150, the valve 5000 can open and close. For example, the magnet 5150 can be moved by using an actuator to open and close the valve 5000. The magnet 5150 can be continually spun in order to activate the valve and facilitate and/or control fluid flow. For example, the valve 5000 can pump fluid from bladder. The valve 5000 can be spun using an actuator to forcibly empty the bladder. The valve 5000 and the actuator 6000 can be configured to allow the user to increase or decrease the flow rate of the urine from the bladder.

Actuator

Figure 7:
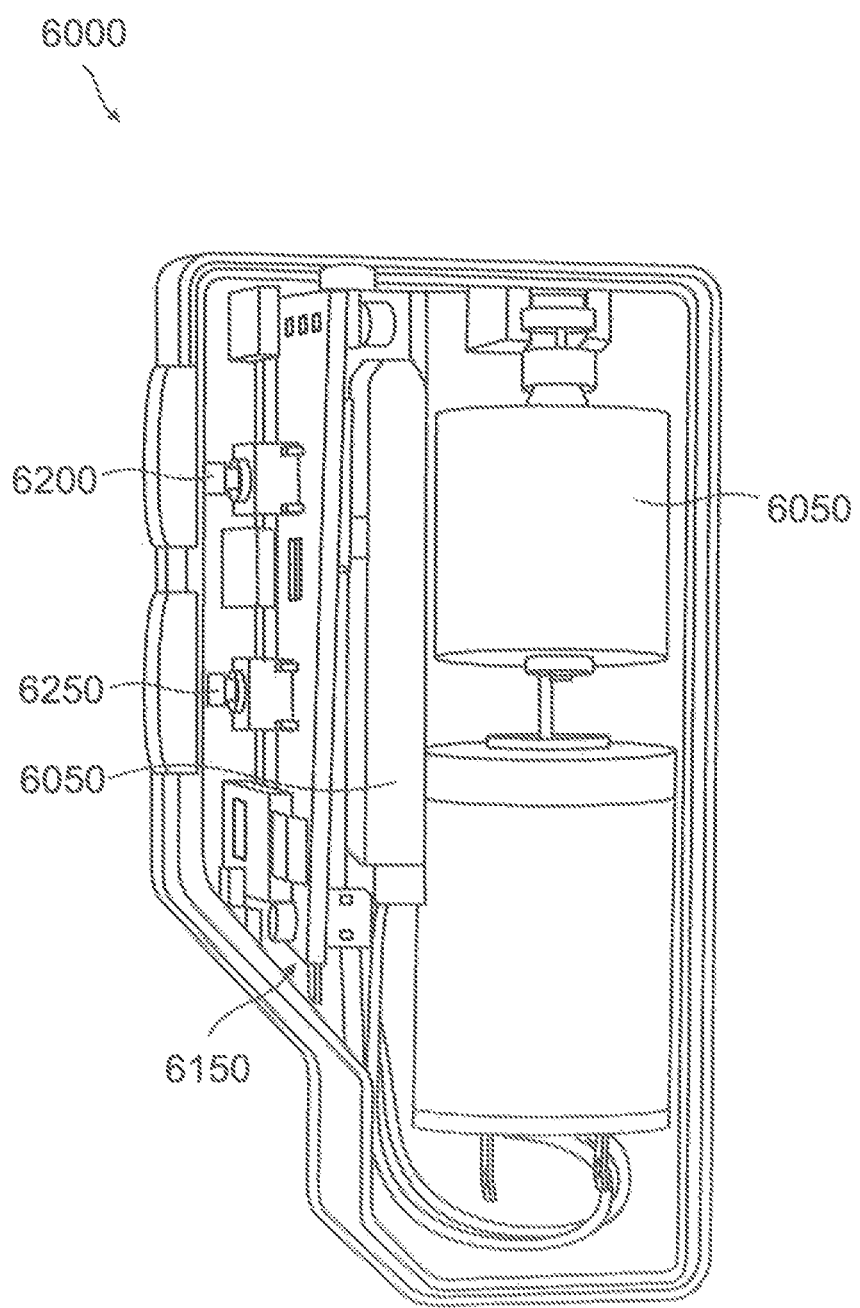
FIG. 7 shows a sample embodiment of a wireless valve actuator.

The urine in the bladder can be voided when the user utilizes an external actuator 6000 to open the valve 5000 and allow the urine to travel through the urethra. As shown in FIG. 7, the actuator 6000 can comprise an actuator magnet 6050, a power source 6100, an electronic circuitry 6150, and one or more inputs 6200, 6250. In some embodiments, the one or more inputs 6200, 6250 can comprise a first input to open the valve and a second input to close the valve 5000. In some embodiments, the circuitry 6150 can comprise software configured to automate process of controlling fluid flow from bladder.

A user can place the external actuator near the valve 2300, e.g. on the skin of patient between the scrotum and the shaft of the penis, as shown in FIG. 2. The user may press the input 6200 to operate the magnet 6050. The actuator can comprise two or more input modes. The valve 2300 can be closed when the actuator 6000 is put on close mode. The valve 2300 can remain closed or remain opened when the actuator 6000 is in off mode.

In some embodiments, the urinary prosthesis system can be configured to detect flow rate of urine through the valve 5000 and the actuator 6000. For example, the system can comprise a software configured to detect the flow rate of urine through the valve 5000 by logging the electric current draw of the motor. For example, the prosthesis system can comprise a an external computing device comprising a memory wirelessly connected to the electronic circuitry

6150 to log operational parameters of the prosthesis system, e.g. flow rate, voiding history, duration, etc.

Retaining Portion

The retaining portion can comprise a collapsible structure configured to collapse and expand when being transported along varying diameters within the urethra. FIG. 8 shows a retaining portion 8400 comprising one or more grooves 8420 and mounds 8410. The retaining portion can comprise a hollow center 8430. The grooves 8420 can be placed along the circumference of the retaining portion. The retaining portion 8400 can comprise alternating grooves 8420 and mounds 8410. For example, the retaining portion 8400 can comprise four grooves 8420 and four mounds 8410 as shown in FIG. 8. The hollow center 8430 can comprise a dimension configured to fit the outer diameter 8370 of the prosthesis.

The retaining portion 8400 can collapse and deploy. The retaining portion 8400 can fold along the grooves 8420 to collapse. The retaining portion 8400 can comprise a rigid material. The retaining portion 8400 can comprise air chamber. The retaining portion can comprise a shape memory material having a pre-programmed shape to expand in response to thermal changes once placed inside the urinary tract.

The retaining portion 8400 can comprise an umbrella structure. The retaining portion 8400 can comprise a balloon with umbrella ribs. In some embodiments, the retaining portion 8400 can comprise a mechanism that can deploy in response to manipulation of the prosthesis. For example, the retaining portion 8400 can be configured to deploy by longitudinally extending the prosthesis using the delivery device. In some embodiments, the retaining portion 8400 can comprise a mechanism that can deploy in response to wireless activation. For example, the retaining portion 8400 comprising magnetic material can be configured to deploy by using a wireless actuator, such as a magnetic actuator.

Materials and Assembly

The prosthesis 1050 and the delivery device 1100 can be constructed in a shape and of a material that is conducive to entry utilizing a medical device. For example, the prosthesis 1050 may be constructed of a material similar to other existing intermittent catheters on the market (such as PVC, Latex, Silicone, Polyurethane or any blend of these materials).

In some embodiments, the method of making the bladder management system 1000 comprises (a) covering a mandrel with an enlargeable portion; (b) connecting the enlargeable portion in a fluid communication to a fluid inlet; (c) placing a first magnet in a first device comprising a chamber, the chamber configured to mate with the enlargeable portion; (d) passing the mandrel with the enlargeable portion through a hole of a second magnet, where the second magnet is configured to magnetically attract and align with the first magnet. The method can further comprise (e) covering the mandrel with the enlargeable portion and the second magnet with a tube, the tube comprising a lumen, such that the second magnet is attached to the tube; (f) connecting a housing handle to the tube to attach the tube to the housing, the housing comprising a cutout and configured to house a portion of the tube and the fluid inlet and restrict longitudinal movement of the fluid inlet relative to the tube; and (g) placing a spring between the tube and the fluid inlet. The method can further comprise (h) placing the first magnet to a portion of the first device; and (i) placing a valve proximal to the first magnet.

Exclusionary Embodiments

Without implying any limitation, the present disclosure can exclude a urinary catheter system that comprises one or more of the following elements, and can also exclude a catheter device that comprises one or more of the following elements. What can be excluded is an element that is, neurostimulator implantable inside body of patient, stimulation pulse generator, leads carrying electrodes, electrode pads, electronic power source placed inside body of patient, circuit systems configured to deliver a therapy protocol, circuit systems configured to deliver stimulation to body tissue, external devices to set stimulation parameters, catheter comprising portions penetrating body tissue, catheter placed under body tissue, catheter requiring surgical incision for placement to body of patient, external device configured to provide neurostimulation, antenna external to the body of patient, tether penetrating body of patient, and so on.

Without implying any limitation, the present disclosure can exclude a urinary catheter system that comprises one or more of the following elements, and can also exclude a catheter device that comprises one or more of the following elements. What can be excluded is an element that is, anchoring means and/or structure placed inside the bladder at the proximal end of a catheter, anchoring means and/or structure contacting at least a portion of the internal ureteral orifice, anchoring means and/or structure contacting at least a portion of the prostate gland, clamp and/or sealing means located on the tip of the penis, tube that projects from the penis and outside of the body of patient, electronic valve opening/closing mechanism, and so on.

In embodiments, the present disclosure can exclude an implant-type device where the implant passes through the prostate but does not extend further into the urethra and contact at least a portion of bulbar urethra; or where portions of the implant does not extend into the bladder; or where the implant does not contain all of: (1) a valve, (2) a mating mechanism for mating with an endoscopic insertion and/or exertion device, and (3) anchoring mechanism configured to be located on or near the bulbar urethra. Also, what can be excluded is a catheter-type device that does not comprise all the above, In embodiments, what can be excluded is a valve which is opened by applying finger pressure against a portion of the valve, such as the distal valve tip; or a valve placed inside patient's body which is opened by applying finger pressure upward toward the prostate; or a squeeze valve where the valve opens and closes using finger pressure. Also, what can be excluded is a mating portion comprising threads, or a device comprising a mating portion comprising threads, where the mating portion is configured to mate with reciprocating threads of another device such as an endoscope.

In embodiments, what can be excluded is a catheter-type device comprising an elongated guiding element and lumen, or a device comprising a tubular elongated guiding element and lumen, or a device comprising a guidewire and lumen, or a device comprising lumen and a retaining element connected to a guiding element, or a device comprising vertebrae inside lumen; or all the above.

What can also be excluded is a urinary catheter device comprising a spheric component, a ferromagnetic sphere, a ball valve comprising a non-ferromagnetic sphere and a ferromagnetic valve seat and/or ferromagnetic conduit, a device comprising a steel sphere with metal comprising Au, Ag, Zn, or Sn. What can be excluded is a urinary catheter device comprising a valve, where the valve opens and closes automatically without manual adjustment with respect to fluid pressure of urine inside the bladder.

What can also be excluded is a urinary catheter device, where the catheter length is over 250 mm. Also, what can be excluded is a urinary catheter device, where the catheter length is under 50 mm. What can also be excluded is a catheter, or a device comprising a catheter, where the catheter length is over 100% of the urethra. What can also be excluded is a urinary catheter device, where the maximum catheter outer diameter is over 7.0 mm. Also, what can be excluded is a urinary catheter device where the maximum catheter outer diameter is under 3.0 mm.

In other embodiments, what can be excluded is a urinary catheter system that comprises one or more of the following elements, and can also exclude an endoscopic device that comprises one or more of the following elements. What can be excluded is a tether connected to the endoscopic device; or a retrieval device comprising a tether, where said tether is connected to a magnet. What can be excluded is an endoscopic device comprising radially expanding basket, radially contracting basket, and so forth.

Also, what can be excluded is a urinary catheter device that comprises one or more of the following elements. What can be excluded is automatic bladder responsive flow control assembly where the assembly is configured to adjust flow rate of urine without manual input. What can be excluded is a urinary catheter device comprising two or more fluid containing compartments, where at least a portion of the compartment is defined by a membrane. What can be excluded is a device comprising a flow control assembly responsive to increased bladder pressure such that fluid is displaced from the first fluid containing compartment to the second fluid containing compartment, where said first fluid containing compartment or the second fluid containing compartment deforms to shuttle fluid from one compartment to another.

In embodiments, what can be excluded is a urinary catheter device that comprises one or more of the following elements. What can be excluded is interposing bridge segment contacting at least a portion of the prostate during use inside patient's body. What can be excluded is a urinary catheter device comprising an interposing bridge segment, where the segment comprises an outer surface comprising materials different from other segments of the catheter. What can be excluded is a urinary catheter device comprising a tubular element coated with a plastic coating. What can be excluded is a urinary catheter device requiring ultrasound for proper placement of the catheter after insertion, where the catheter is echogenic.

In embodiments, what can be excluded is a urinary catheter device comprising two or more mandrels. What can be excluded is valve element configured to pivot away or towards the valve seat in a sealing relation.

Without implying any limitation, the present disclosure can exclude a urinary catheter system that comprises one or more of the following elements, and can also exclude a device that comprises one or more of the following elements. In embodiments, what can be excluded is a urinary catheter device comprising valve residing in the shaft of the penis, balloon located in the bladder, inflatable urethra cuff. What can be excluded is a catheter device comprising drainage member separate from catheter, two or more inflation lumens, and so forth.

In embodiments, what can be excluded is a urinary catheter device comprising an anchoring mechanism blocking the fluid channel or the lumen of the catheter. What can be excluded is anchoring mechanism which provides prevention of only either of retrograde or antegrade catheter migration.

Among the many advantages of this invention include increasing the qualify of life for individuals suffering from neurogenic bladder by: 1. reducing the risk of medical issues (urinary tract infections, false passage, etc.); 2. eliminating the need for indwelling or intermittent catheters and decreasing the number of catheters required for daily use (because of increased accuracy with which the user knows when catheterization is required); 3. allowing the user to control bladder voiding; 4. accommodating implanted, semi-permanent (useful life 3-6 months) device via minimally invasive means (via catheter); 5. minimizing problems from incontinence and related psychological impact (emotional trauma from accidental urinary voiding); and 6. transmits wireless report data similar to that done in urodynamic flow testing (pressure of bladder at different levels of fullness) more accurately and less invasively.

Although embodiments of the invention have been shown and described, it is to be understood that various modifications, substitutions, rearrangements and different parts, components, equipment, elements and/or process (method) steps, as well as other uses, of the wireless pressure sensor and valve for bladder can be made by those skilled in the art without departing from the novel spirit and scope of this invention.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

"Circuitry", as used in any embodiment herein, may comprise, for example, singly or in any combination, hard-wired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Unless otherwise indicated, all numbers expressing quantities of ingredients, properties such as molecular weight, reaction conditions, and so forth used in the specification and claims are to be understood as being modified in ail instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristics). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A bladder management system comprising an extended use prosthesis and device for transporting the extended use prosthesis within a body of a patient, the system comprising:
    an extended use prosthesis comprising an elongated tubular body comprising an outer dimension and configured to be placed inside a urinary tract of a patient's body and invisible to human eyes from outside of the body once inside the urinary tract, the extended use prosthesis comprising:
    a first mating structure on or near a distal end of the prosthesis;
    a retaining portion comprising a maximum cross-sectional dimension greater than the outer dimension of the tubular body of the prosthesis;
    a valve portion placed between the first mating structure and the retaining portion and configured to control passage of fluid from a bladder of the patient through the prosthesis; and
    a transporting device comprising a handle and a second mating structure, the handle located on or near a distal end of the transporting device, the second mating structure placed on or near a proximal end of the transporting device and configured to mate with the first mating structure:
    wherein at least a portion of the retaining portion is placed within a bulbar urethra of the patient once the prosthesis is placed inside the urinary tract;
    wherein the first mating structure comprises a mating chamber;
    wherein the second mating structure comprises a second configuration and a third configuration, wherein in the third configuration the second mating structure is mated to the first mating structure and in the second configuration the second mating structure is removable from the first mating structure;
    wherein the second mating structure comprises a deployable portion and when the second mating structure is in a first configuration the deployable portion remains substantially hidden inside a lumen of the transporting device while in the second and the third configurations the deployable portion is exposed outside of the lumen of the transporting device;
    wherein the transporting device comprises a fluid inlet and the deployable portion comprises a balloon configured to inflate and deflate by increasing and decreasing a fluid inside the balloon through the fluid inlet, wherein the balloon is exposed outside the lumen by moving the fluid inlet relative to the handle;
    wherein the transporting device comprises:
    an outer lumen connected to the handle and comprising an outer longitudinal length from the handle to a proximal end of the outer lumen, the outer longitudinal length being greater than a length from a membranous portion to a urethral orifice of a patient; and a mandrel placed inside the outer lumen and comprising a mandrel longitudinal length greater than the outer longitudinal length of the outer lumen;
    wherein the second mating structure comprises one or more magnets.

2. The system of claim 1, wherein the fluid is introduced and removed to and from the balloon via the fluid inlet using a syringe device.

3. A bladder management system comprising an extended use prosthesis and device for transporting the extended use prosthesis within a body of a patient, the system comprising:
an extended use prosthesis comprising an elongated tubular body comprising an outer dimension and configured to be placed inside a urinary tract of a patient's body and invisible to human eyes from outside of the body once inside the urinary tract, said extended use prosthesis comprising:
a first mating structure on or near a distal end of the prosthesis;
a retaining portion comprising a maximum cross-sectional dimension greater than the outer dimension of the tubular body of the prosthesis;
a valve portion placed between the first mating structure and the retaining portion and configured to control passage of fluid from a bladder of the patient through the prosthesis; and
a transporting device comprising a handle and a second mating structure, the handle located on or near a distal end of the transporting device, the second mating structure placed on or near a proximal end of the transporting device and configured to mate with the first mating structure;
wherein at least a portion of the retaining portion is placed within a bulbar urethra of the patient once the prosthesis is placed inside the urinary tract;
wherein the first mating structure comprises a mating chamber;
wherein the second mating structure comprises a second configuration and a third configuration, wherein in the third configuration the second mating structure is mated to the first mating structure and in the second configuration the second mating structure is removable from the first mating structure;
wherein the second mating structure comprises a deployable portion and when the second mating structure is in a first configuration the deployable portion remains substantially hidden inside a lumen of the transporting device while in the second and the third configurations the deployable portion is exposed outside of the lumen of the transporting device;
wherein the transporting device comprises a fluid inlet and the deployable portion comprises a balloon configured to inflate and deflate by increasing and decreasing a fluid inside the balloon through the fluid inlet, wherein the balloon is exposed outside the lumen by moving the fluid inlet relative to the handle;
wherein the transporting device comprises:
an outer lumen connected to the handle and comprising an outer longitudinal length from the handle to a proximal end of the outer lumen, the outer longitudinal length being greater than a length from a membranous portion to a urethral orifice of a patient; and
a mandrel placed inside the outer lumen and comprising a mandrel longitudinal length greater than the outer longitudinal length of the outer lumen;
wherein the second mating structure comprises one or more magnets;
wherein the one or more magnets comprise a first magnet comprising a first diameter and a second magnet comprising a second diameter less than the first diameter.

4. The system of claim 3, wherein the fluid is introduced and removed to and from the balloon via the fluid inlet using a syringe device.

5. A bladder management system comprising an extended use prosthesis and device for transporting the extended use prosthesis within a body of a patient, the system comprising:
an extended use prosthesis comprising an elongated tubular body comprising an outer dimension and configured to be placed inside a urinary tract of a patient's body and invisible to human eyes from outside of the body once inside the urinary tract, said extended use prosthesis comprising:
a first mating structure on or near a distal end of the prosthesis;
a retaining portion comprising a maximum cross-sectional dimension greater than the outer dimension of the tubular body of the prosthesis;
a valve portion placed between a first mating structure and the retaining portion and configured to control passage of fluid from a bladder of the patient through the prosthesis; and
a transporting device comprising a handle and a second mating structure, the handle located on or near a distal end of the transporting device, the second mating structure placed on or near a proximal end of the transporting device and configured to mate with the first mating structure;
wherein at least a portion of the retaining portion is placed within a bulbar urethra of the patient once the prosthesis is placed inside the urinary tract;
wherein the first mating structure comprises a mating chamber;
wherein the second mating structure comprises a second configuration and a third configuration, wherein in the third configuration the second mating structure is mated to the first mating structure and in the second configuration the second mating structure is removable from the first mating structure:
wherein the second mating structure comprises a deployable portion and when the second mating structure is in a first configuration the deployable portion remains substantially hidden inside a lumen of the transporting device while in the second and the third configurations the deployable portion is exposed outside of the lumen of the transporting device;
wherein the transporting device comprises a fluid inlet and the deployable portion comprises a balloon configured to inflate and deflate by increasing and decreasing a fluid inside the balloon through the fluid inlet, wherein the balloon is exposed outside the lumen by moving the fluid inlet relative to the handle;
wherein the transporting device comprises:
an outer lumen connected to the handle and comprising an outer longitudinal length from the handle to a proximal end of the outer lumen, the outer longitudinal length being greater than a length from a membranous portion to a urethral orifice of a patient; and
a mandrel placed inside the outer lumen and comprising a mandrel longitudinal length greater than the outer longitudinal length of the outer lumen;
wherein the second mating structure comprises one or more magnets; wherein the one or more magnets comprise a first magnet comprising a first diameter and a second magnet comprising a second diameter less than the first diameter;
wherein, the prosthesis comprises a prosthesis magnet placed proximal to the mating chamber along the tubular body of the prosthesis, the prosthesis magnet configured to attract and concentrically align with the one or more magnets.

6. The system of claim 5, wherein the fluid is introduced and removed to and from the balloon via the fluid inlet using a syringe device.

* * * * *